United States Patent
Yamamoto et al.

(10) Patent No.: US 9,453,819 B2
(45) Date of Patent: Sep. 27, 2016

(54) ULTRASONIC FLAW DETECTOR AND ULTRASONIC FLAW DETECTING METHOD

(75) Inventors: Setsu Yamamoto, Yokohama (JP); Takahiro Miura, Yokohama (JP); Jun Semboshi, Yokohama (JP); Makoto Ochiai, Yokohama (JP); Satoshi Nagai, Kawasaki (JP); Kazumi Watanabe, Yokohama (JP); Tadahiro Mitsuhashi, Yokohama (JP); Hiroyuki Adachi, Machida (JP); Satoshi Yamamoto, Kawaguchi (JP); Junichi Takabayashi, Yokohama (JP); Masaru Otsuka, Ota-Ku (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 673 days.

(21) Appl. No.: 13/548,810

(22) Filed: Jul. 13, 2012

(65) Prior Publication Data

US 2013/0014587 A1 Jan. 17, 2013

(30) Foreign Application Priority Data

Jul. 15, 2011 (JP) ................................. 2011-157056

(51) Int. Cl.
*G01N 29/24* (2006.01)
*G01N 29/04* (2006.01)
*G01N 29/26* (2006.01)

(52) U.S. Cl.
CPC .......... *G01N 29/043* (2013.01); *G01N 29/262* (2013.01); *G01N 2291/056* (2013.01); *G01N 2291/2638* (2013.01)

(58) Field of Classification Search
CPC ............. G01N 29/043; G01N 29/262; G01N 2291/2638; G01N 2291/056
USPC .................... 73/602, 633, 634, 640
See application file for complete search history.

(56) References Cited

U.S. PATENT DOCUMENTS

| | | | | | |
|---|---|---|---|---|---|
| 4,235,111 | A | * | 11/1980 | Hassler | A61B 8/4494 367/105 |
| 6,200,267 | B1 | * | 3/2001 | Burke | G01S 7/52046 600/443 |
| 7,594,439 | B2 | * | 9/2009 | Fischer et al. | 73/626 |

(Continued)

FOREIGN PATENT DOCUMENTS

JP 2006-47328 A 2/2006
JP 2007-170877 A 7/2007

OTHER PUBLICATIONS

Extended European Search Report issued on Jun. 6, 2014 in the corresponding European Application No. 12176468.2.
(Continued)

*Primary Examiner* — Laura Martin
*Assistant Examiner* — Rose M Miller
(74) *Attorney, Agent, or Firm* — Oblon, McClelland, Maier & Neustadt, L.L.P

(57) ABSTRACT

An ultrasonic flaw detector including an ultrasonic probe for emitting an ultrasonic wave on an object to be inspected and receiving a reflected ultrasonic wave from the object, a drive element control unit for controlling a plurality of ultrasonic elements to emit an ultrasonic wave from the ultrasonic probe and to control a reflected ultrasonic wave from the object, and a calculation unit for obtaining, by using a refraction angle of the ultrasonic wave at a time of the ultrasonic wave entering the object, an incident position of the ultrasonic wave on a surface of the object, and a surface shape of a surface of the object at the incident position, the incident angle of the ultrasonic wave entering the incident position, and obtaining a plurality of ultrasonic elements to be driven, based on the incident position and the incident angle.

8 Claims, 17 Drawing Sheets

(56) References Cited

U.S. PATENT DOCUMENTS

| | | | |
|---|---|---|---|
| 2004/0050166 A1* | 3/2004 | Batzinger | G01N 29/069 73/614 |
| 2010/0251822 A1* | 10/2010 | Isobe et al. | 73/606 |
| 2011/0000299 A1* | 1/2011 | Isobe et al. | 73/625 |
| 2011/0000300 A1* | 1/2011 | Isobe et al. | 73/625 |

OTHER PUBLICATIONS

S. Mahaut, et al., "An adaptive system for advanced NDT applications using phased arrays", Ultrasonics, IPC Science and Technology Press L td., vol. 36, No. 1-5, XP004119500, Feb. 1, 1998, pp. 127-131.

* cited by examiner

ULTRASONIC FLAW DETECTOR AND ULTRASONIC FLAW DETECTING METHOD

BACKGROUND OF THE INVENTION

1. Field of the Invention

The present invention relates to an ultrasonic flaw detector and an ultrasonic flaw detecting method.

2. Description of the Related Art

Ultrasonic flaw detection testing is a non-destructive technology that enables checking of the soundness of the surface and the inside of a construction material, and is a testing technology indispensable in various fields. Especially, in recent years, there is a demand for testing of a construction having a complex surface shape such as a curved surface, and the technological demand regarding ultrasonic flaw detection is becoming higher.

In the case an object to be inspected has a complex surface shape, there is a problem that an ultrasonic wave cannot be appropriately emitted on the object. For example, at a weld line and its heat-affected zone, a portion which is designed to be planar unintentionally becomes non-planar due to a strain or chevron-like deformation caused by welding heat input or a convex shape formed after molten metal is poured.

Furthermore, various piping structures typified by a nozzle stub of, for example, a nuclear power plant or a thermal power plant, or a platform region of a turbine blade is designed to have a complex shape, and even if constructed as designed, testing thereof is difficult. If such object is taken as the object of the ultrasonic flaw detection testing, an ultrasonic wave cannot be emitted on the object or, even if the ultrasonic wave is emitted, a desired refraction angle may not be obtained.

In contrast, a phased array (PA) is a technology of forming a given waveform by arranging small ultrasonic sensors, and varying the timing (delay time) of the sensors and emitting ultrasonic waves. Compared to a monolithic probe that can only emit ultrasonic waves at a predetermined angle, the phased array can possibly cope with a complex shape.

However, with the phased array technology, the delay time reflecting the shape has to be calculated for each target. Further, the value of the shape to be reflected should include not only the values on a drawing, but also the as-built values (a drawing created based on existing conditions and analysis data). Accordingly, to carry out ultrasonic flaw detection on a complex-shaped region, a technology for measuring the surface shape of a target with high accuracy is needed, as well as a technology for controlling ultrasonic waves (calculating the delay time) according to the curvature.

To solve the above matters, there is conventionally proposed a method which measures the surface shape of an object by an ultrasonic probe, optimizes the transmission delay time of the PA according to the measured shape, and conducts testing (for example, Japanese Patent Laid-Open No. 2007-170877: Patent Document 1).

However, the Patent Document 1 only describes optimization of delay time conditions according to the surface shape of an object. Therefore, when using an electronic scan, which, typified by a linear scan, sequentially moves elements to be used, elements to be used are fixed with respect to a focal point, and thus, there arises a problem that an ultrasonic wave enters from an unintended incident point. There is also provided a problem of an ultrasonic wave not reaching a test portion due to use of an element at a blind angle.

On the other hand, emitting an ultrasonic wave according to the surface shape allows to cope with the problem of the incident angle of the ultrasonic wave changing. However, at the time of displaying a flaw detection result, a flaw indication echo is displayed at a portion different from the actual detection position in a flaw detection result that is displayed in a case if analysis has been performed without taking the influence of the surface shape into consideration.

The position of an indication echo cannot be accurately identified unless the flaw detection result is separately corrected in consideration of the influence of the surface shape, and an error occurs in the detection position. That is, the flaw detection accuracy is greatly reduced. It is also conceivable that an indication echo is extended and is displayed with a shape different from the actual flaw. This can be overcome if an inspector corrects the detection position error by hand calculation while taking the influence of the surface shape into consideration. But this will increase the burden on the inspector. In addition, if the surface shape is complex, correction will require much skill.

SUMMARY OF THE INVENTION

The present invention has been made in view of the above circumstances, and an object thereof is to provide an ultrasonic flaw detector and a method thereof, which are capable of achieving high detecting accuracy regardless of the surface shape of an object.

An embodiment of the ultrasonic flaw detector of the present invention provided for solving the problems described above includes an ultrasonic probe that emits an ultrasonic wave on an object to be inspected and receiving a reflected ultrasonic wave from the object, a drive element control unit that controls a plurality of ultrasonic elements to emit an ultrasonic wave on the ultrasonic probe and to control a reflected ultrasonic wave from the ultrasonic probe, and a calculation unit that obtains, by using a refraction angle of the ultrasonic wave incident in the object, an incident position of the ultrasonic wave on a surface of the object and a surface shape of a surface of the object at the incident position, the incident angle of the ultrasonic wave entering the incident position, and that obtains a plurality of ultrasonic elements to be driven, based on the incident position and the incident angle.

Furthermore, an embodiment of the ultrasonic flaw detecting method of the present invention provided for solving the problems described above includes the steps of emitting an ultrasonic wave on an object to be inspected by driving a plurality of ultrasonic elements and receiving a reflected ultrasonic wave from the object, determining a refraction angle of the ultrasonic wave incident in the object and an incident position of the ultrasonic wave on a surface of the object, acquiring a surface shape of a surface of the object at the incident position, obtaining an incident angle of the ultrasonic wave entering the incident position, based on the refraction angle, the incident position, and the surface shape, and obtaining a plurality of ultrasonic elements to be driven, based on the incident position and the incident angle.

With the ultrasonic flaw detection and the method thereof according to the embodiments of the present invention can achieve high detection accuracy regardless of the surface shape of an object to be inspected.

BRIEF DESCRIPTION OF THE DRAWINGS

FIG. 12 is an explanatory diagram of a case of the ultrasonic flaw detector obtaining center coordinates Ec of simultaneously driven elements and the like;

DESCRIPTION OF THE PREFERRED EMBODIMENTS

An embodiment of an ultrasonic flaw detector according to the present invention and a method thereof will be described hereunder with reference to the accompanying drawings.

Figure 1:
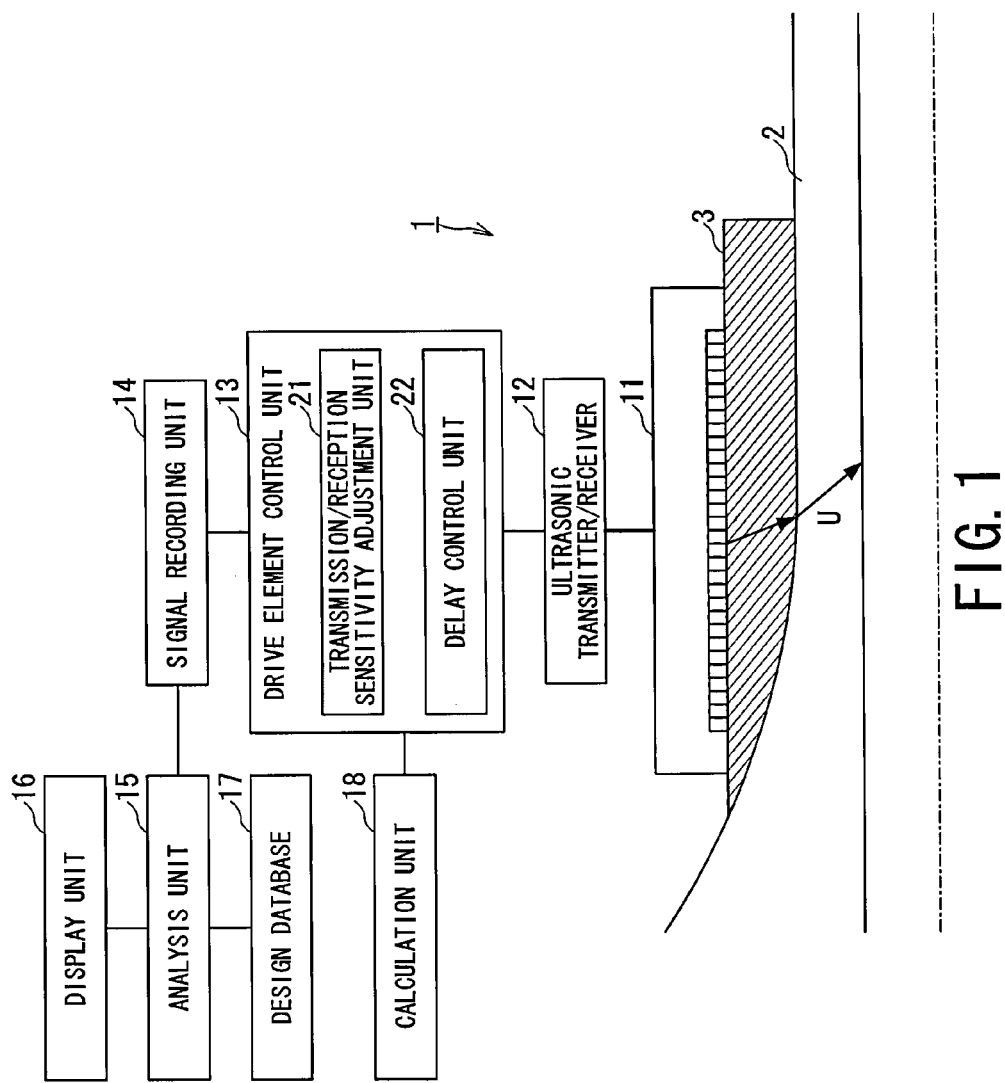
FIG. 1 is a functional block diagram showing a configuration of an embodiment of an ultrasonic flaw detector according to the present invention.

FIG. 1 is a functional block diagram illustrating a configuration of an embodiment of the ultrasonic flaw detector according to the present invention. According to the present embodiment, an object to be detected is a pipe 2, and an example will be described with reference to a case in which flaw detection using ultrasonic waves is conducted to a flaw portion of the pipe 2. The dotted line in FIG. 1 indicates the center of the pipe.

The ultrasonic flaw detector of the present example is basically provided with an ultrasonic probe, and, in association with the ultrasonic probe, an ultrasonic transmitter/receiver and a drive element control unit for controlling a drive element, and a calculation unit for calculating control information of the drive element.

More specifically, an ultrasonic flaw detector 1 is generally composed of an ultrasonic probe 11, and, in association with the ultrasonic probe, an ultrasonic transmitter/receiver 12 for transmitting/receiving ultrasonic waves and a drive element control unit 13 for controlling a drive element, and a calculation unit 18 for calculating information for the drive element control unit 13 to control a drive element. Furthermore, as described later, the ultrasonic flaw detector 1 connected to the drive element control unit 13 is provided with a signal recording unit 14, an analysis unit 15, a display unit 16, and a design database 17.

The ultrasonic probe 11 is a well-known ultrasonic probe that transmits/receives ultrasonic waves U. The ultrasonic probe 11 emits an ultrasonic wave U on the pipe 2 via acoustic coupling medium 3 by driving a plurality of ultrasonic elements, and receives a reflected ultrasonic wave from the pipe 2. The acoustic coupling medium 3 is a medium that is capable of propagating an ultrasonic wave, such as water, glycerin, machine oil, acrylic gel, or polystyrene gel, for example. Further, in the present embodiment, illustration of the acoustic coupling medium 3 may be sometimes omitted.

The ultrasonic probe 11 has ultrasonic elements that are one-dimensionally arranged and is generally referred to as a linear array sensor.

The ultrasonic probe 11 includes, for example, a mechanism for generating an ultrasonic wave, a damping material for damping an ultrasonic wave, and a front plate attached to a plane of oscillation of an ultrasonic wave. The mechanism for generating an ultrasonic wave is, for example, ceramics or ceramic composite materials, or a piezoelectric element that generates an ultrasonic wave by piezoelectric effect, or a piezoelectric element formed of a polymer film.

Furthermore, the ultrasonic probe may be a 1.5-dimensional array sensor in which elements are unequally divided in the depth direction of a linear array sensor, a matrix array sensor in which elements are two-dimensionally arranged, or a ring array sensor in which ring-shaped elements are concentrically arranged. The ultrasonic probe may also be a divided ring array sensor in which the elements of a ring array sensor are divided in the circumferential direction, a random array sensor in which elements are randomly arranged, an arc array sensor in which elements are arranged at positions in the circumferential direction of an arc, a spherical array sensor in which elements are arranged on the surface of a sphere, or any other array sensor.

Hereunder, the function of each of the structural elements described above will be explained. The ultrasonic transmitter/receiver 12 is connected to the ultrasonic probe 11, and handles transmission/reception of an ultrasonic wave. The drive element control unit 13 controls an ultrasonic element that is to be actually driven at the ultrasonic transmitter/receiver 12 in response to drive control information for an ultrasonic element calculated by the calculation unit 18. The drive element control unit 13 includes a transmission/reception sensitivity adjustment unit 21, and a delay control unit 22, in which the transmission/reception sensitivity adjustment unit 21 adjusts transmission/reception sensitivity for an ultrasonic wave from the ultrasonic transmitter/receiver 12. On the other hand, the delay control unit 22 controls the oscillation of each of a plurality of ultrasonic elements according to a given time.

Furthermore, the signal recording unit 14 stores a received signal (ultrasonic signal) received by the drive element control unit 13.

The analysis unit 15 analyzes the received signal stored in the signal recording unit 14 and calculates a flaw detection result. Specifically, the analysis unit 15 calculates the flaw detection result based on the propagation path of an ultrasonic wave obtained on the basis of the surface information of the pipe 2 on which the ultrasonic wave is emitted. That is, the analysis unit 15 obtains the propagation path of the ultrasonic wave using a relative angle between the surface, of the pipe 2, at a position in which the ultrasonic wave is emitted and the ultrasonic probe 11.

The display unit 16 displays the flaw detection result obtained by the analysis unit 15. The design database 17 that is connected to the analysis unit 15 stores in advance data on the surface shape of the pipe 2 at the stage of design.

Furthermore, the ultrasonic flaw detector 1 is not limited to the configuration mentioned above as long as it adds delay time to the ultrasonic probe composed of a plurality of piezoelectric elements and controls the transmission/reception of ultrasonic waves. Moreover, a flaw detecting method of performing transmission/reception delay control of ultrasonic waves using a plurality of piezoelectric elements such as a phased array is well known, and hence, a detailed explanation thereof is omitted.

When installing the ultrasonic probe 11, a wedge may be used to use an angle with a high degree of directivity. The wedge is an isotropic material that allows propagation of an ultrasonic wave and where acoustic impedance is grasped. The wedge is formed from acrylic, polyimide, gel or any other polymer materials, for example. Further, in order to prevent the influence of a multiply reflected wave within the wedge on a flaw detection result, damping materials may be arranged within and outside the wedge, a mountain-shaped wave-absorbing form may be provided, or a mechanism for multiple reflection reduction may be provided.

Next, a flaw detecting method that uses a basic phased array (PA) will be described.

Figure 2:
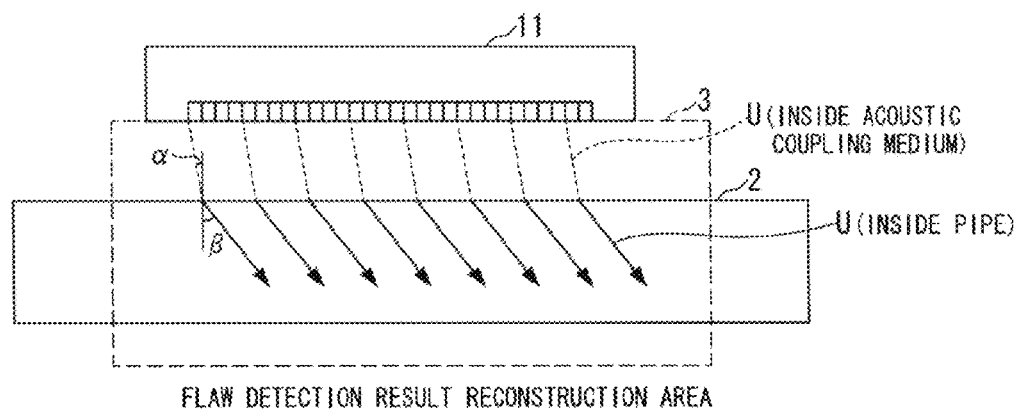
FIG. 2 is an explanatory diagram showing an example of general flaw detection.
Figure 3:
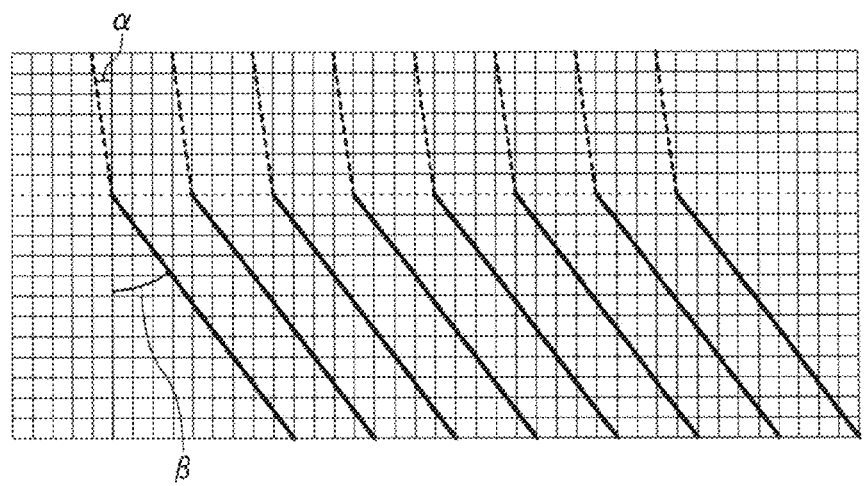
FIG. 3 is an explanatory diagram showing an example of general reconstruction of a flaw detection result.

FIG. 2 is an explanatory diagram showing an example of basic flaw detection, and FIG. 3 is an explanatory diagram showing an example of basic reconstruction of a flaw detection result.

With reference to FIGS. 2 and 3, to emit ultrasonic waves U into the pipe 2 at a given refraction angle β and focal positions, a plurality of ultrasonic elements (piezoelectric elements) provided to the ultrasonic probe 11 of the PA are given with appropriate delay time and are then oscillated. The direction and focal positions of the ultrasonic waves are thereby controlled.

If there is a reflector such as a flaw inside the pipe 2, an ultrasonic wave U emitted into the pipe 2 is reflected and dispersed. The reflected ultrasonic wave is received by an ultrasonic element of the ultrasonic probe 11. The waveform of the received ultrasonic wave is imaged in the direction of the electronic scan according to an incident angle α and the refraction angle β of the ultrasonic wave which have been set.

This imaging is generally referred to as B-scan or S-scan. As shown in FIG. 3, an image is reconstructed based on the incident angle α and the refraction angle β that are according to the flaw detection conditions at the time of flaw detection. In the following explanation, the B-scan will be is used.

Figure 4:
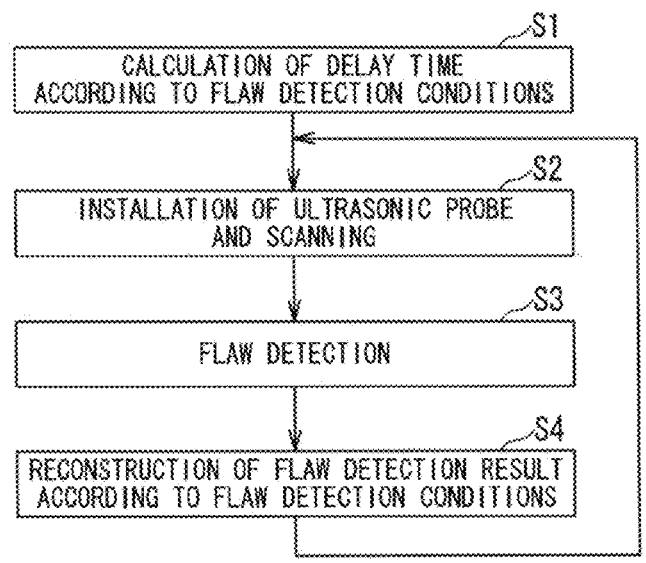
FIG. 4 is a flow chart showing a general flaw detecting method.

Herein, a basic flaw detecting method will be described using the flow chart of FIG. 4.

First, delay time is calculated according to flaw detection conditions such as the refraction angle β and the focal position on the pipe 2 (step S1). Then, the ultrasonic probe 11 is installed above the pipe 2, and scanning is started (step S2).

Flaw detection is conducted on the pipe 2 according to the scanning (step S3), and data on the waveform of the ultrasonic wave obtained according to the flaw detection conditions such as the refraction angle β is reconstructed, and a B-scan is prepared (step S4). Thereafter, the scanning position of the pipe 2 is changed, and steps from the installation/operation step S2 to the reconstruction step S4 are repeated.

Here, if the flaw detection step S3 and the reconstruction step S4 are performed under flaw detection conditions assuming a planarity condition in a case where there is a curved surface such as an undulation (a partial curve) due to excessive weld metal or grinding (FIG. 5) or in a case the pipe 2 is not planar from the start, an ultrasonic wave does not enter at an intended angle. In addition, an error occurs in the detection result.

Figure 5:
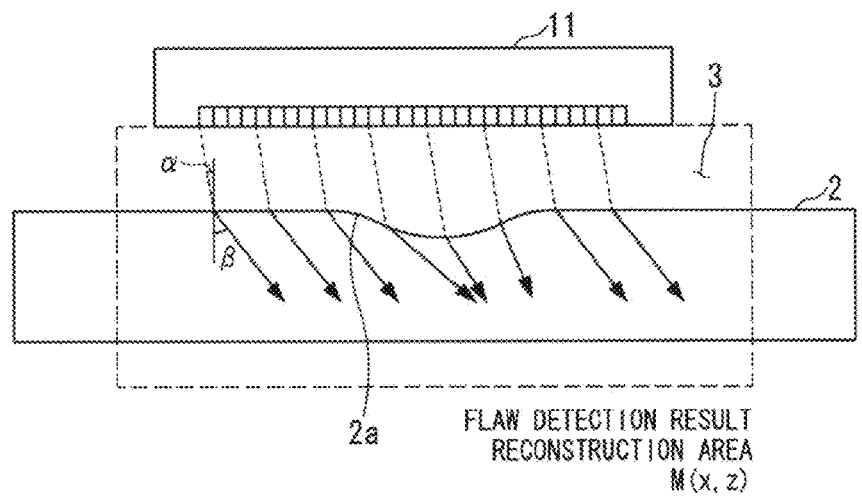
FIG. 5 is an explanatory diagram of flaw detection testing where a curved surface is formed on the surface of a pipe.

FIG. 5 is an explanatory diagram of the flaw detection testing in which a curved surface 2a is formed on the surface of the pipe 2.

In the case where the calculation is performed under the flaw detection conditions assuming a planarity condition as shown in FIG. 2, the flaw detection is conducted with the incident angle α from any position of the ultrasonic probe 11. Therefore, if an ultrasonic wave is emitted on the surface of the pipe 2 having a curved surface 2a such as an undulation, the refraction angle β is not fixed due to Snell's law, and the propagation path of an ultrasonic wave varies depending on the incident position.

The above process prevents not only the flaw detection with an intended ultrasonic wave, but also, depending on the incident angle α, the emission of an ultrasonic wave on the pipe 2. Further, in the case of evaluating a received ultrasonic signal, if reconstruction is conducted under the planarity condition without taking the surface shape of the pipe 2 into consideration, deviation from the actual propagation path of an ultrasonic wave will occur.

This point will be described in greater detail hereunder.

Figure 6:
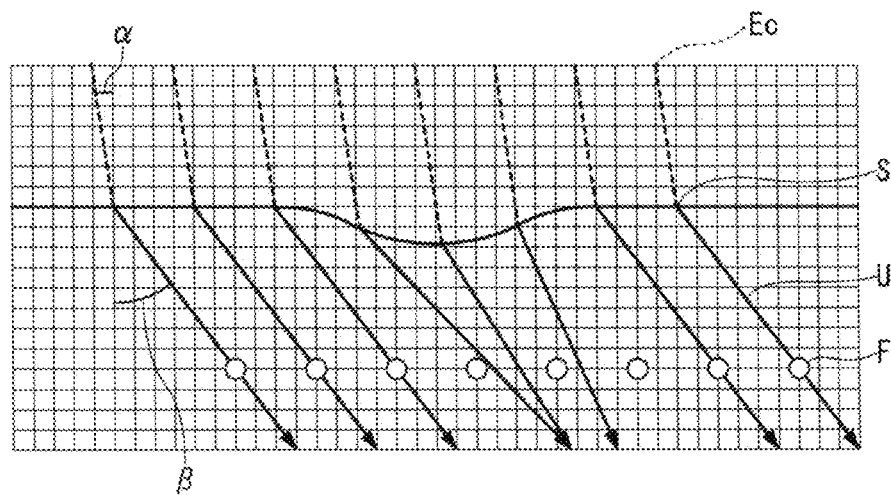
FIG. 6 is an explanatory diagram of an ultrasonic wave propagation path where flaw detection is conducted without taking the surface shape of a pipe into consideration.
Figure 7:
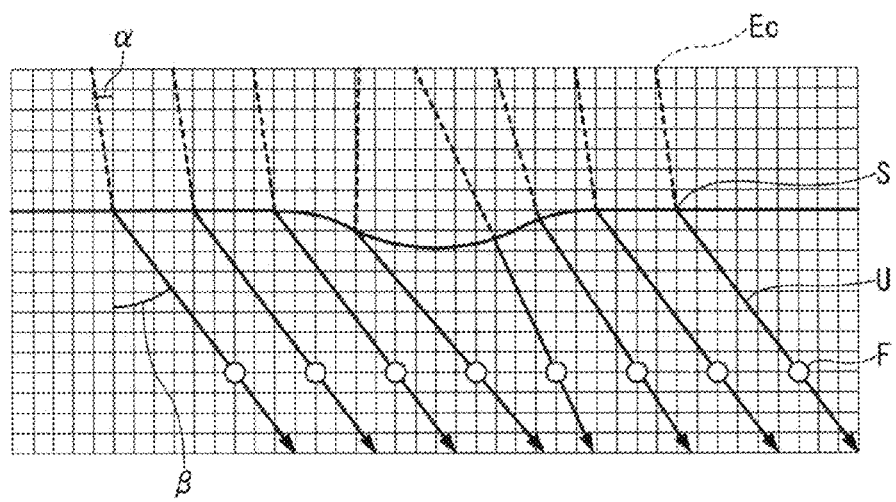
FIG. 7 is an explanatory diagram of an ultrasonic wave propagation path where flaw detection is conducted, taking the surface shape of a pipe into consideration.

FIG. 6 is an explanatory diagram of an ultrasonic wave propagation path where the flaw detection is conducted without taking the surface shape of the pipe 2 into consideration. FIG. 7 is an explanatory diagram of an ultrasonic wave propagation path where the flaw detection is conducted, taking the surface shape of the pipe 2 into consideration.

As shown in FIG. 6, ultrasonic waves U are transmitted under a condition assuming that the surface of the pipe 2 is a planar surface. In this case, the incident angles α are uniform, but the refraction angles β become non-uniform under the influence of the surface shape and the incident ultrasonic waves will follow paths different from the intended path. A flaw position obtained by the reconstruction will include an error with respect to the actual position of a flaw existing on the pipe 2, which will result in an error or overlooking in the evaluation of a flaw detection result.

In FIG. 7, the surface shape of the pipe 2 is taken into consideration, and the delay time is controlled such that an ultrasonic wave enters a focal point F of the pipe 2. With a general linear scan, the combination of ultrasonic elements that are simultaneously used (simultaneously driven elements) is decided in advance. These simultaneously driven elements move sequentially. The constants in the conditions for the flaw detection are the center position Ec of the simultaneously driven elements which are the starting points of the ultrasonic waves and the focal points F within the pipe 2 which are the goal points, and the parameters are incident points S.

That is, also in this case, the refraction angles β are not necessarily uniform, and a general requirement for ultrasonic testing adopted by standards (such as JIS) that "flaw detection testing is conducted with uniform refraction angles β" is not satisfied. Furthermore, depending on the surface shape of the pipe 2, an element that may not properly emit an ultrasonic wave is possibly unavoidably used, and an ultrasonic wave of sufficient intensity may not be emitted.

In contrast to the ultrasonic flaw detection technology as described above, the ultrasonic flaw detector 1 of the present embodiment, in consideration of the surface shape of the pipe 2, can suitably emit ultrasonic waves on the pipe 2 and also make the refraction angles β uniform.

An ultrasonic wave propagation path in a case of conducting flaw detection by the ultrasonic flaw detector 1 of the present embodiment will be described with reference to FIG. 8.

Figure 8:
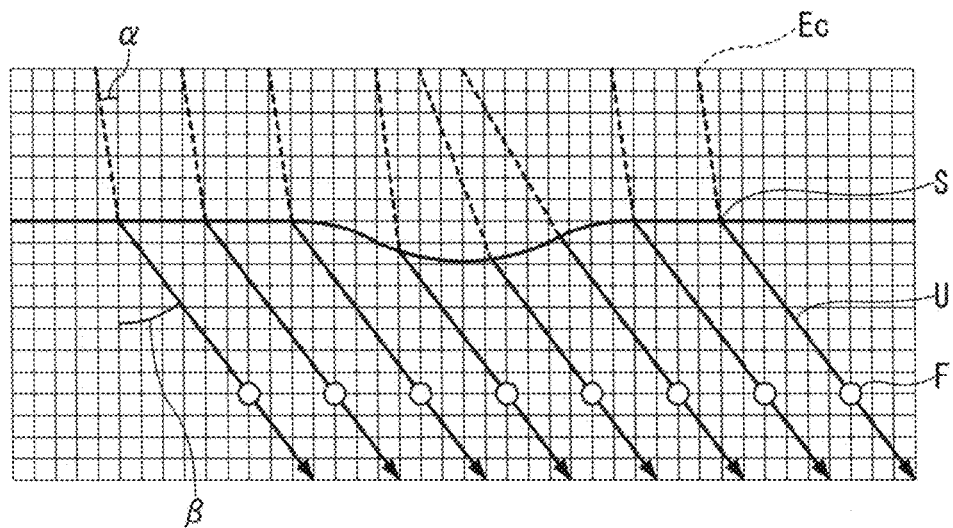
FIG. 8 is an explanatory diagram showing an ultrasonic wave propagation path where flaw detection is conducted by an ultrasonic flaw detector according to the present embodiment.

With reference to FIG. 8, the ultrasonic flaw detector 1 conducts the flaw detection by calculating control information regarding an ultrasonic element by the calculation unit 18, and driving the ultrasonic element by the drive element control unit 13 based on the control information. Specifically, the incident points S and the focal points F are made constants based on the known surface shape of the pipe 2 and desired refraction angles β, and optimal ultrasonic elements are back calculated with the center position Ec of the simultaneously driven elements as a parameter. The ultrasonic flaw detector 1 uses the obtained ultrasonic elements and the performs the flaw detection by controlling the delay time of the ultrasonic elements. The ultrasonic flaw detector 1 can thereby always maintain uniform refraction angles β.

Herein now, a flaw detecting method of the ultrasonic flaw detector 1 of the present embodiment will be described.

Figure 9:
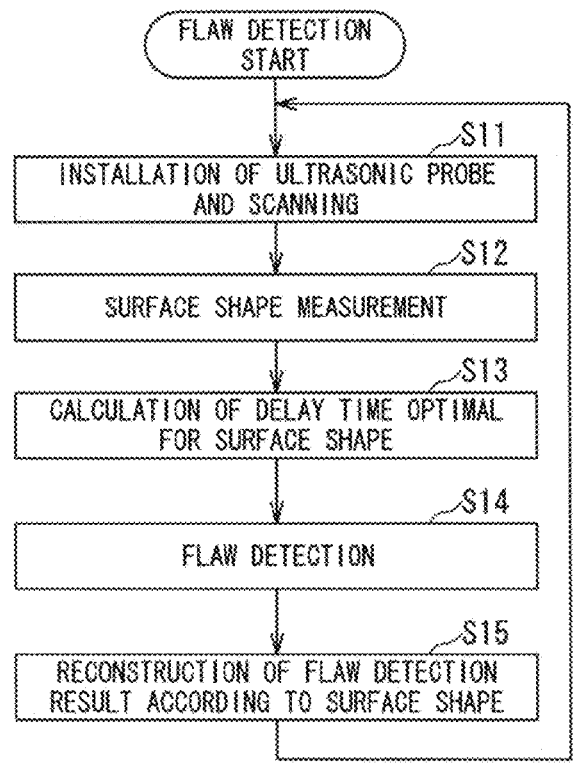
FIG. 9 is a flow chart describing a concept of a flaw detecting method of the ultrasonic flaw detector of the present embodiment.

FIG. 9 is a flow chart describing an overview of a flaw detecting method of the ultrasonic flaw detector 1 of the present embodiment.

First, the ultrasonic probe 11 is installed above the pipe 2 and scanning is started (step S11), and the surface shape of the pipe 2 is measured using a shape measuring device (step S12). The surface shape may be obtained by measuring the as-built shape, or by importing the measurement data stored in the design database 17. The details of the shape acquisition step S12 will be described later.

Next, in step S13, the delay control unit 22 calculates the optimal delay time for an ultrasonic element with respect to the surface shape, the ultrasonic probe 11 conducts the flaw detection on the pipe 2 (step S14), the ultrasonic data according to the surface shape is reconstructed, and a B-scan is generated (step S15).

Further, for generation of a flaw detection result reconstruction area M, there are conceivable a method of calculating the position on a flaw detection result M from an ultrasonic signal Uj, and a method of calculating the position of an ultrasonic signal Uj corresponding to the coordinates from the coordinate points on the flaw detection result M.

Thereafter, the installation step S11 to the reconstruction step S15 are repeated until the flaw detection is completed.

Hereunder, a process for obtaining center coordinates (the center position Ec in FIG. 8) of simultaneously driven elements used for flaw detection will be described.

Figure 10:
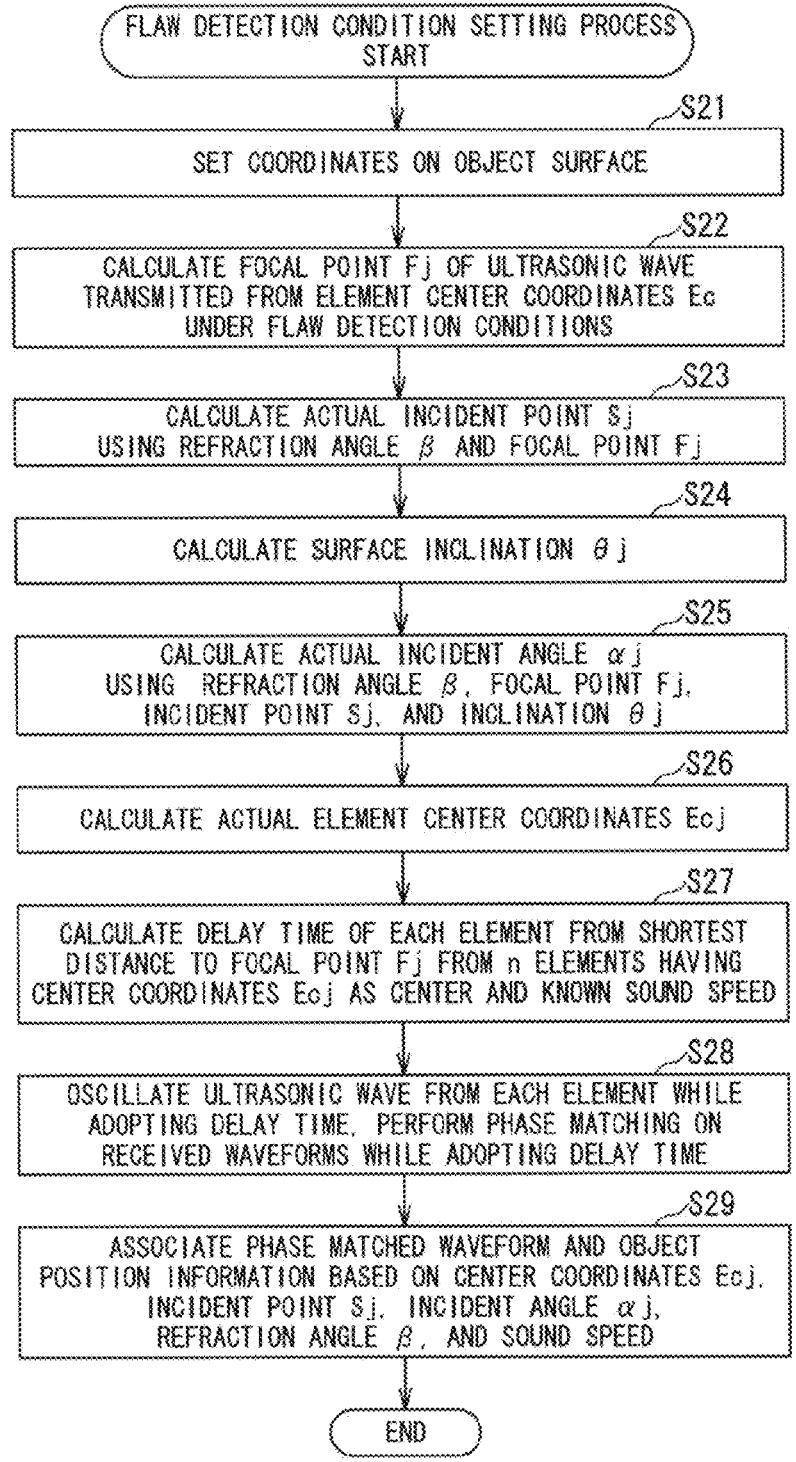
FIG. 10 is a flow chart describing a flaw detection condition setting process conducted by the ultrasonic flaw detector of the present embodiment.
Figure 11:
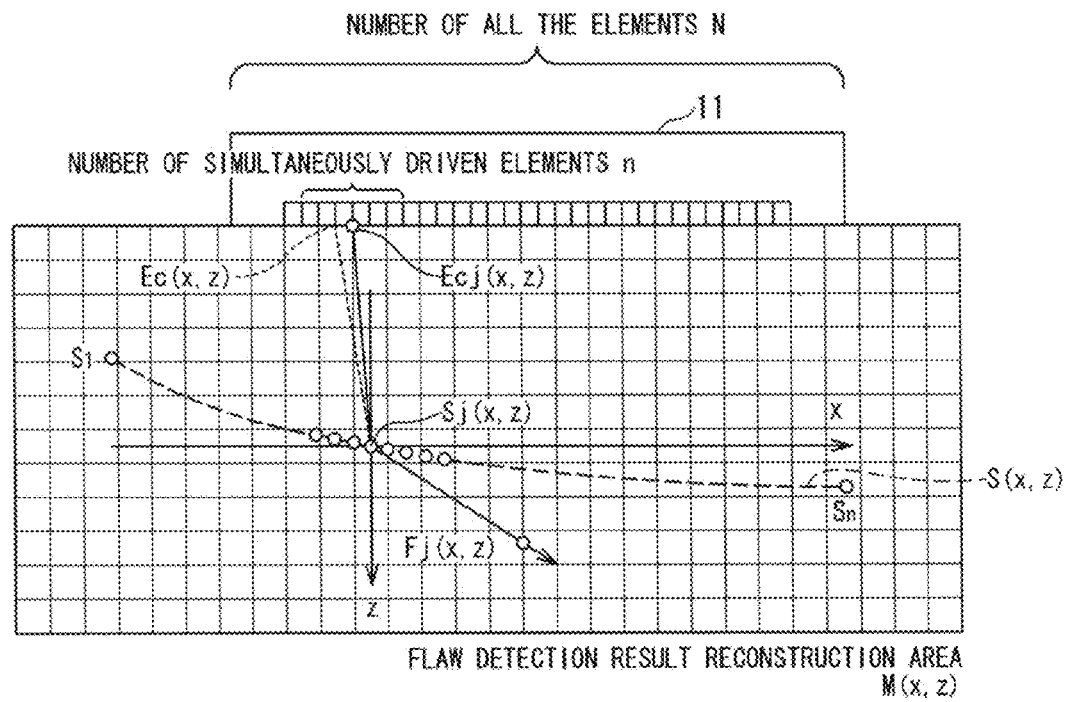
FIG. 11 is an explanatory diagram showing a state of propagation of an ultrasonic wave in a pipe.
Figure 12:
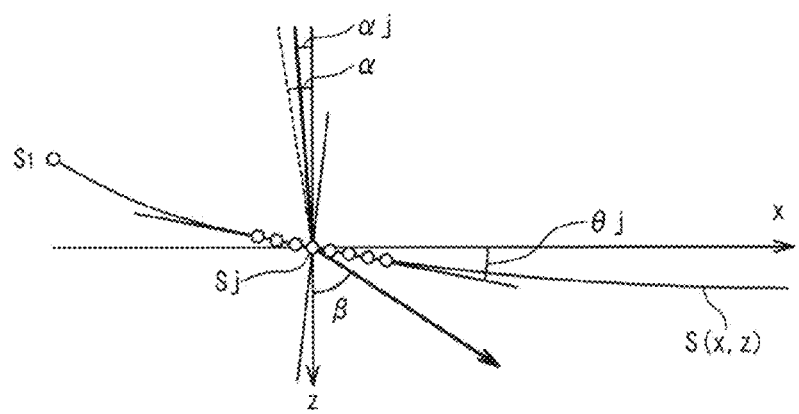

FIG. 10 is a flow chart describing a flaw detection condition setting process conducted by the ultrasonic flaw detector 1 of the present embodiment. FIG. 11 is an explanatory diagram showing a state of propagation of an ultrasonic wave in the pipe 2. FIG. 12 is an explanatory diagram of a case of the ultrasonic flaw detector 1 obtaining center coordinates Ec of simultaneously driven elements and the like.

In the present embodiment, an explanation will be given taking a linear array probe as a representative example, and thus, coordinate information will be expressed in two dimensions (x, z). If a probe with two-dimensionally arranged piezoelectric elements, such as a matrix array, is used, it will be set in three dimensions (x, y, z).

When the coordinates of each element are $Ei(x, z)$ (i=1, 2, ..., N), and the number of simultaneously driven elements is n ($1 \leq n \leq N$), elements from the element coordinates Ei to element coordinates Ei+n will be used for flaw detection. The element center coordinates of all the simultaneously driven elements is $Ec(x, z)$. Here, the coordinates of the surface shape of the pipe 2 are given by a surface shape function $S(x, z)$. A sequence j (pattern) of the flaw detection is performed up to 'm' times on the surface shape function S, and a focal point where ultrasonic waves converge is taken as $Fj(x, z)$.

The focal point Fj is a focal point of an ultrasonic wave which has entered an assumed plane from the center coordinates Ec of the simultaneously driven elements at the incident angle α and refracted at the refraction angle β converging at a set depth. The surface shape coordinates where a straight line with the refraction angle β passing through the focal point Fj intersects with the surface shape function S is taken as Sj (incident point Sj). The inclination of the surface of the pipe 2 at the surface shape coordinates Sj (the relative angle between the ultrasonic probe 11 and the surface of the pipe 2) is taken as θj.

Next, a flaw detection condition setting process conducted by the ultrasonic flaw detector 1 of the present embodiment will be described with reference to the flow chart of FIG. 10.

In the flaw detection condition setting process, first, the ultrasonic flaw detector 1 sets coordinates on the pipe surface (step S21). Specifically, the ultrasonic flaw detector 1 determines the element coordinates Ei of the ultrasonic probe 11, and determines a surface shape function S based on the measurement result or the design data of the surface shape of the pipe 2.

Then, the ultrasonic flaw detector 1 calculates the focal point Fj of the ultrasonic wave transmitted from the simultaneously driven elements with the center coordinates Ec, using the flaw detection conditions used in the linear scanning (normal linear scanning) that is conducted when the surface shape of the pipe 2 is assumed to be planar (step S22). More specifically, the ultrasonic flaw detector 1 transmits an ultrasonic wave from the center coordinates Ec at an incident angle α, causes the propagation inside the pipe 2 at a refraction angle β obtained when assuming that the ultrasonic wave entered the pipe 2 having a planar shape, and assumes that a point reached at a desired convergence depth of the ultrasonic wave as the focal point Fj.

Furthermore, the ultrasonic flaw detector 1 calculates an incident point Sj that is according to the actual surface shape, using the refraction angle β and the focal point Fj (step S23). Specifically, the ultrasonic flaw detector 1 draws a straight line of the refraction angle β passing through the focal point Fj, and takes the point of intersection of the straight line and the surface shape function S as the incident point Sj. The ultrasonic flaw detector 1 further calculates an inclination θj at the incident point Sj (step S24). The calculation method of the inclination θj will be described later in detail.

The ultrasonic flaw detector 1 calculates the actual incident angle αj (the incident angle taking the surface shape into consideration) by using Snell's law and by using the focal point Fj, the refraction angle β, the incident point Sj, and the inclination θj which have been calculated, and known sound speed values in the acoustic coupling medium 3 and the pipe 2 (step S25). The actual incident angle αj is a parameter in the ultrasonic flaw detecting method of the present embodiment.

The ultrasonic flaw detector 1 calculates the actual center coordinates Ecj (the center coordinates of simultaneously driven elements taking the surface shape into consideration) using the incident point Sj and the incident angle αj (step S26). Specifically, the ultrasonic flaw detector 1 draws a straight line from the incident point Sj with an inclination of the angle αj, and assumes that the center coordinates Ec closest to the straight line as Ecj.

Then, the ultrasonic flaw detector 1 calculates by numerical calculation, for each of 'n' elements having the center coordinates Ecj as the center, the shortest distance between the element coordinates Ei and the focal point Fj through the surface shape function S. The ultrasonic flaw detector 1 obtains the propagation time of each ultrasonic wave from a known sound speed, and calculates the difference from the minimum value as the delay time of each element (step S27).

Next, the ultrasonic flaw detector 1 conducts the flaw detection using the calculated delay time and adds up the waveforms received by the elements while reflecting the delay time. The ultrasonic flaw detector 1 thereby obtains a phase matched waveform Uj(t) (step S28).

Figure 13:
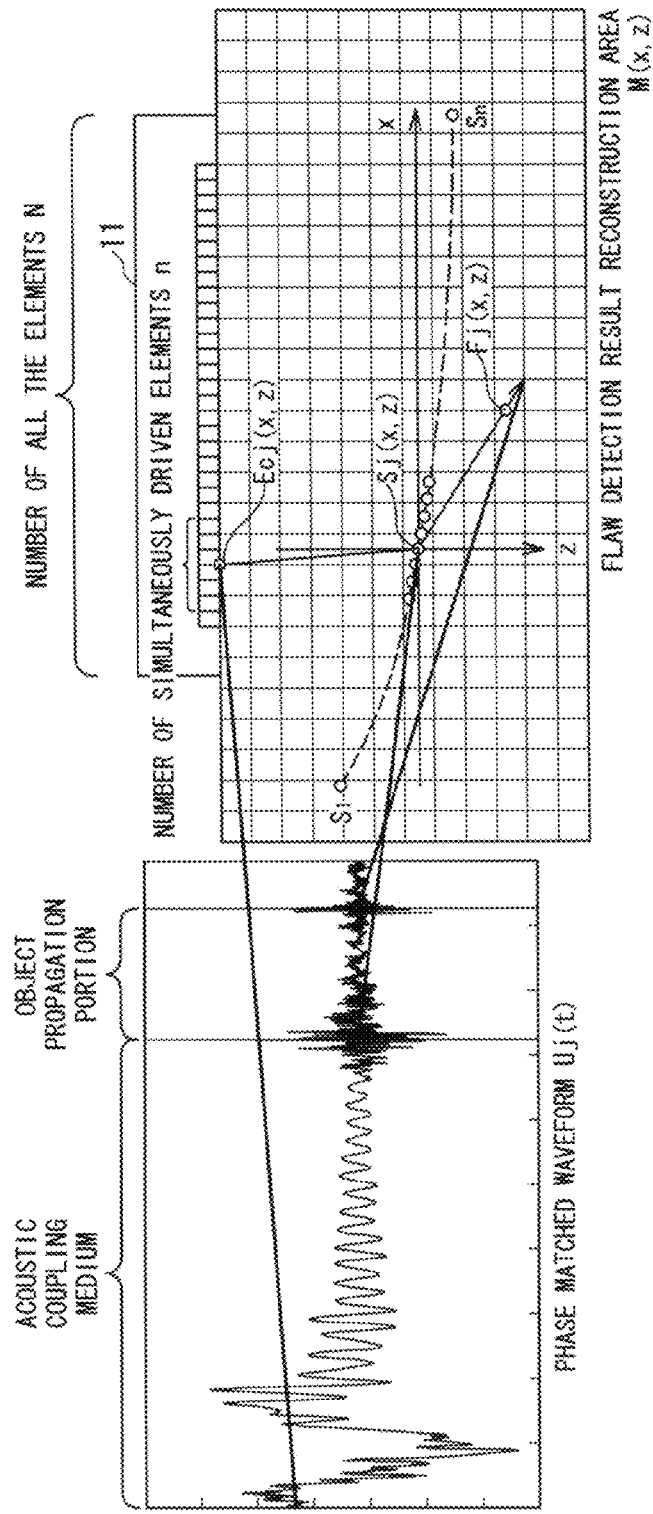
FIG. 13 is an explanatory diagram showing an example of a phase matched waveform Uj(t) obtained by the ultrasonic flaw detector according to the present embodiment.

An explanation will be given with reference to an explanatory diagram of FIG. 13 showing an example of the phase matched waveform Uj(t) obtained by the ultrasonic flaw detector 1 according to the present embodiment. The ultrasonic flaw detector 1 associates the phase matched waveform Uj(t) and position information regarding the pipe 2 using the center coordinates Ecj, the incident point Sj, the focal point Fj, the refraction angle β, the incident angle αj, and the sound speeds of the acoustic coupling medium 3 and the pipe 2 (flaw detection conditions) (step S29).

Specifically, the ultrasonic flaw detector 1 calculates the ultrasonic wave propagation time using the flaw detection conditions described above, and obtains the intensity of the phase matched waveform Um(t) corresponding to a flaw detection result reconstruction area M(x, z). The ultrasonic flaw detector 1 can obtain a flaw detection result which has been reconstructed by plotting the intensity of a waveform Um corresponding to the coordinates M.

The ultrasonic flaw detector 1 scans the ultrasonic probe 11 and installs it at the next flaw detection position, repeats the coordinate setting step S21 to the associating step S29, and obtains a similar flaw detection result at the next flaw detection position.

Figure 14:
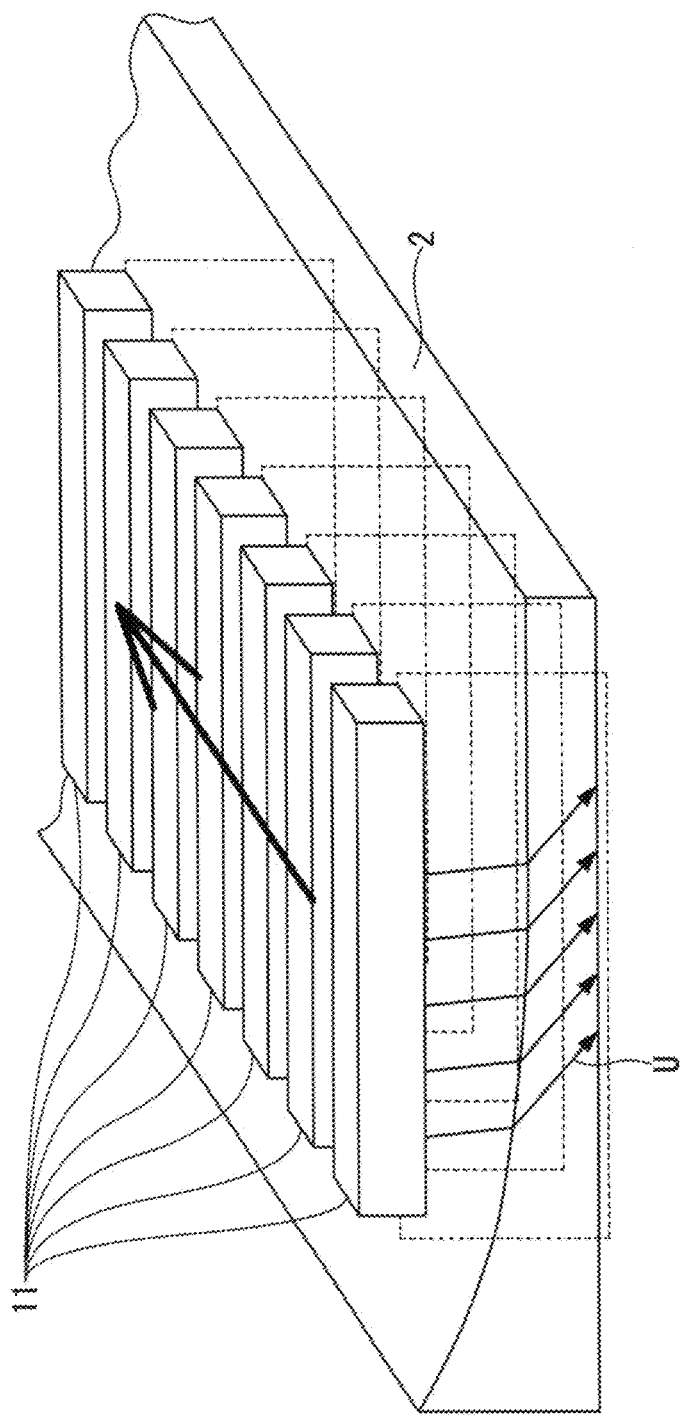
FIG. 14 is an explanatory diagram of a case where an ultrasonic probe performs scanning.

FIG. 14 is an explanatory diagram of a case where the ultrasonic probe 11 performs scanning.

When a linear array is adopted as the ultrasonic probe 11, the ultrasonic flaw detector 1 scans the ultrasonic probe 11 in a direction orthogonal to the direction of the lined up arrays. The ultrasonic flaw detector 1 can thereby obtain a three-dimensional flaw detection result. A similar result can be also obtained by conducting the scanning in a given direction in the case when other probes such as a matrix probe and a ring array probe are adopted.

Herein, a method of obtaining the inclination θj of the surface of the pipe 2 at the surface shape coordinates Sj will be described, in which the inclination θj is a relative angle between the ultrasonic probe 11 and the surface of the pipe 2.

Figure 15:
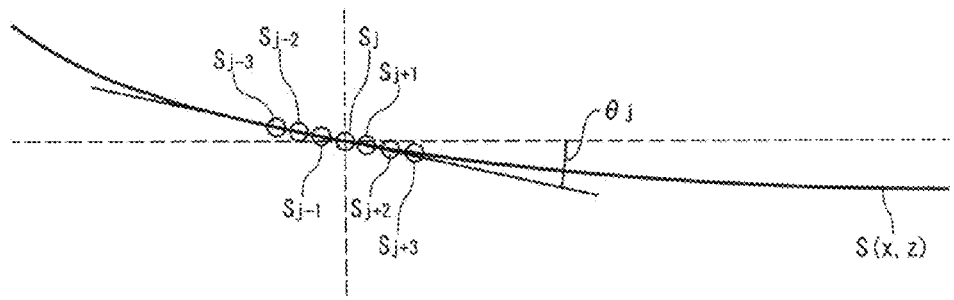
FIG. 15 is an explanatory diagram of a case of obtaining an inclination θj of a pipe surface.

Referring to FIG. 15, an explanation will be given for a case of obtaining the inclination θj of the surface of the pipe 2.

The inclination θj at the incident point Sj of an ultrasonic wave is calculated from surface shape coordinates Sj−1 and Sj+1 adjacent to the incident point Sj. The inclination θj can also be calculated using surface shape coordinates Sj−a and Sj+a that are apart from the incident point Sj by 'a'. The inclination θj can also be calculated by using each point from the surface shape coordinates Sj−a to Sj+a and performing linear approximation by a method such as a least squares method so as to pass through each point.

Figure 16:
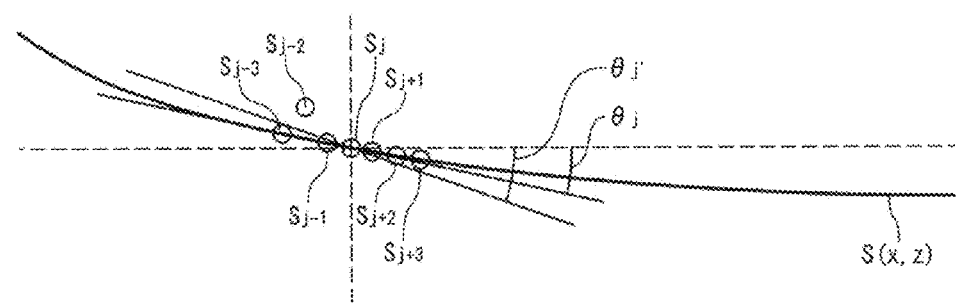
FIG. 16 is another explanatory diagram of a case of obtaining an inclination θj of a pipe surface.

FIG. 16 is another explanatory diagram of a case of obtaining the inclination θj of the surface of the pipe 2.

Since noise sometimes occurs in the shape measurement result, if all the pieces of data are used, θj' with an error with respect to the actual inclination θj may be calculated. For this reason, the inclination θj may be calculated after removing data points that are highly deviated among a plurality of points from the surface shape coordinates Sj−a to Sj+a.

Furthermore, when identifying the incident point Sj from the center coordinates Ecj, certain surface shape coordinates Sk, and the focal point Fj, the inclination θj at each position of the surface shape function S may be calculated first. In this case, the calculation is performed with respect to the center coordinates Ecj, the certain surface shape coordinates Sk, and the focal point Fj from coordinates S1 to coordinates Sn, according to Snell's law. A value with a minimum absolute value of the measurement result can be taken as the incident point Sj in the positional relationship of the center coordinates Ecj, the certain surface shape coordinates Sk, and the focal point Fj.

Figure 17:
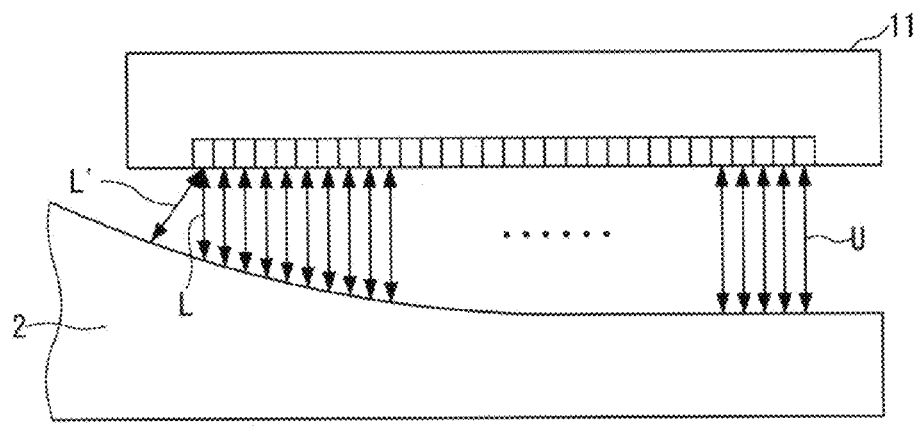
FIG. 17 is an explanatory diagram of a method of measuring a surface shape function that uses a flight time method.
Figure 18:
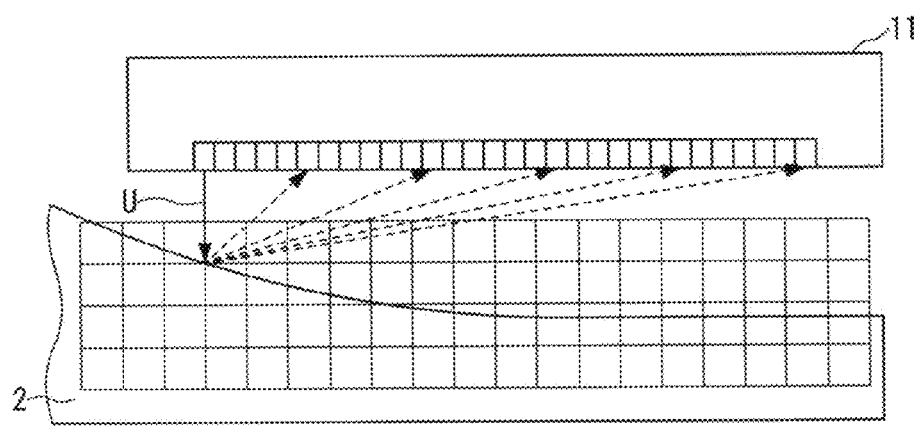
FIG. 18 is an explanatory diagram of a method of measuring a surface shape function that uses aperture synthesis.

Next, an explanation will be given on the method of measuring the surface shape function S of the pipe 2 with reference to FIGS. 17 and 18. FIG. 17 is an explanatory diagram of a method of measuring the surface shape function that uses a flight time method. FIG. 18 is an explanatory diagram of a method of measuring the surface shape function that uses aperture synthesis.

The flight time method is a method of receiving an ultrasonic wave U transmitted from an ultrasonic element (element coordinates Ei) by the same ultrasonic element and reconstructing the shape of the surface of the pipe 2 from the propagation time of the received echo.

On the other hand, with the aperture synthesis method, a process of transmitting an ultrasonic wave U from an ultrasonic element (element coordinates Ei) and receiving the reflected wave by all the elements at element coordinates E1 to EN is performed. An element used for transmission is changed sequentially from the element coordinates E1 to EN, and the surface shape is measured using the measurement data. At this time, not all the pieces of the waveform data have to be used for the aperture synthesis process, and arbitrary data may be selected and be used for the process.

Figure 19:
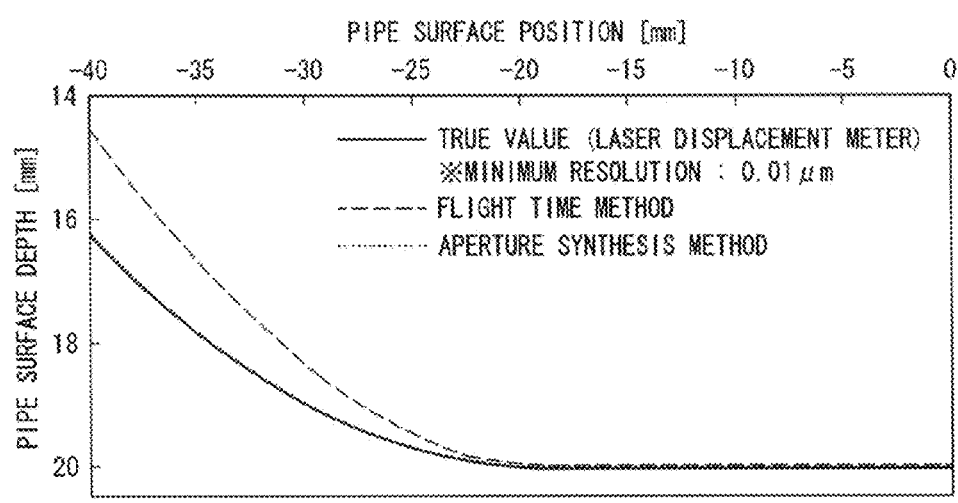
FIG. 19 is a graph showing comparison between the surface shape functions obtained by the methods of FIGS. 17 and 18 and a true value.

FIG. 19 is a graph showing comparison between the surface shape functions obtained by the methods of FIGS. 17 and 18 and a true value.

The surface shape of the pipe 2 which is the true value was measured by a laser displacement meter. Measurement was performed with high accuracy by the aperture synthesis method, but it was found out that the error is great at the curvature portion according to the flight time method. This is because, with the flight time method, an echo is picked up whose propagation path is not the intended sound ray L but a shortest distance L'. Accordingly, the flight time method is not suitable for measurement of a complex surface shape.

However, since, compared to the aperture synthesis method, the amount of data and the signal processing time can be greatly reduced, the flight time method is effective with an object with a small curvature or when grasping the relative position of the ultrasonic probe and the object, for example.

For measurement of the surface shape function, other methods of measuring the surface shape by using the ultrasonic probe 11 can also be adopted, such as a method of adopting a delay time according to which the focal point is on the surface of the object and measuring the shape of the surface from the delay time, and a method of plotting concentrically the echoes obtained by the flight time method for each element and connecting the tangents.

An explanation will be given on a result of simulating the ultrasonic wave propagation path in a case where the ultrasonic flaw detector 1 of the present embodiment is used.

Figure 20:
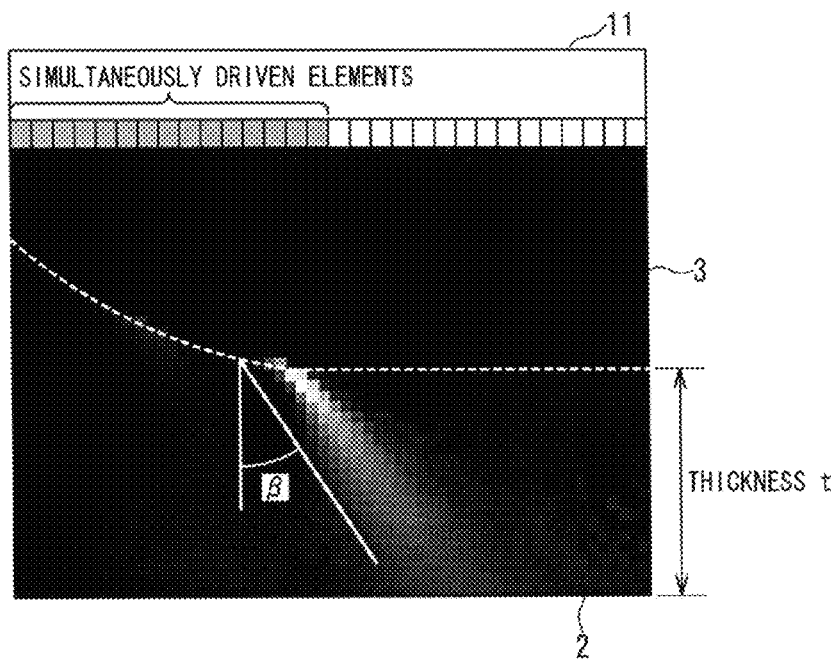
FIG. 20 is a diagram showing a result of simulation performed under predetermined conditions for the intensity of an ultrasonic wave assuming that the surface shape is planar.
Figure 21:
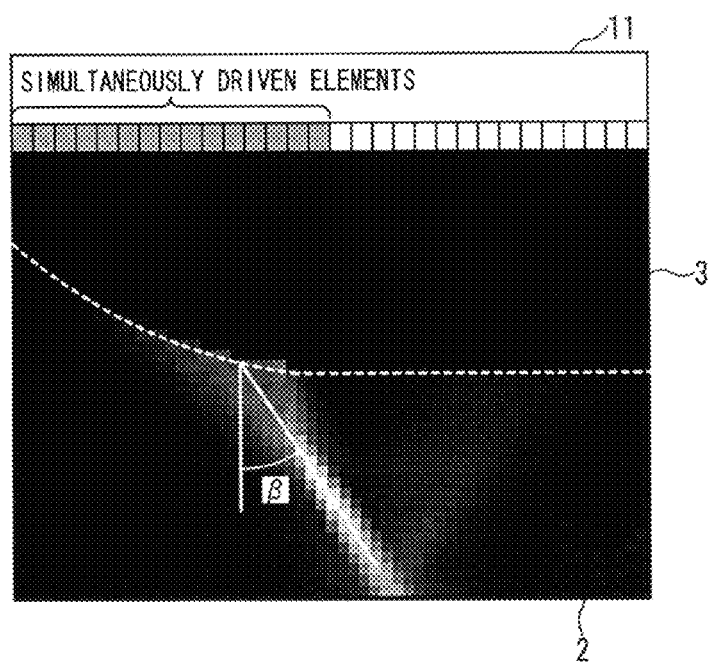
FIG. 21 is a diagram showing a result of simulation performed under predetermined conditions for the intensity of an ultrasonic wave assuming that the surface shape is curved.

FIG. 20 is a diagram showing a result of simulation performed under predetermined conditions for the intensity of an ultrasonic wave assuming that the surface shape is planar. FIG. 21 is a diagram showing a result of simulation performed under predetermined conditions for the intensity of an ultrasonic wave assuming that the surface shape is curved.

The transmission delay conditions for the ultrasonic probe 11 are the refraction angle β of 45 degrees and the focal point forming position of ¾t with respect to the thickness t of the pipe 2. In FIGS. 20 and 21, the intensity of an ultrasonic wave is shown based on sound field simulation for a case where the ultrasonic wave is emitted on the surface of the pipe 2 having a curved surface.

As shown in FIG. 20, although the ultrasonic wave enters the pipe 2 from a part of a planar surface 2b of the surface of the pipe 2, it does not sufficiently enter from a curved surface 2a. On the other hand, as shown in FIG. 21, in the case of emitting the ultrasonic wave under the transmission delay conditions according to the curved surface 2a, the ultrasonic wave enters the pipe 2 also from the curved surface 2a.

The ultrasonic flaw detector 1 can maintain the constant flaw detection conditions inside the pipe 2 by controlling, according to the surface shape of the pipe 2, the incident angle at each incident point such that the flaw detection conditions inside the pipe 2 are the same. Furthermore, the ultrasonic flaw detector 1 can emit the ultrasonic wave onto the curved surface 2a where flaw detection was not possible in FIG. 20.

Hereunder, there is described a result of taking a test object that simulates an undulation of a weld portion and has a flaw as an object, and conducting the flaw detection by the ultrasonic flaw detector 1 of the present embodiment, and reconstructing the obtained ultrasonic signal.

Figure 22:
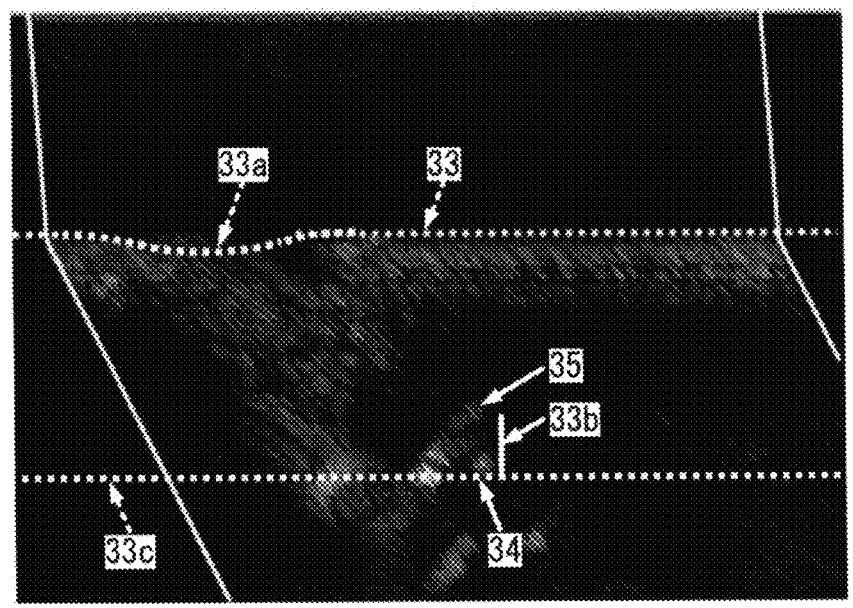
FIG. 22 is a diagram showing a result of performing reconstruction without taking the surface shape of an object into consideration.
Figure 23:
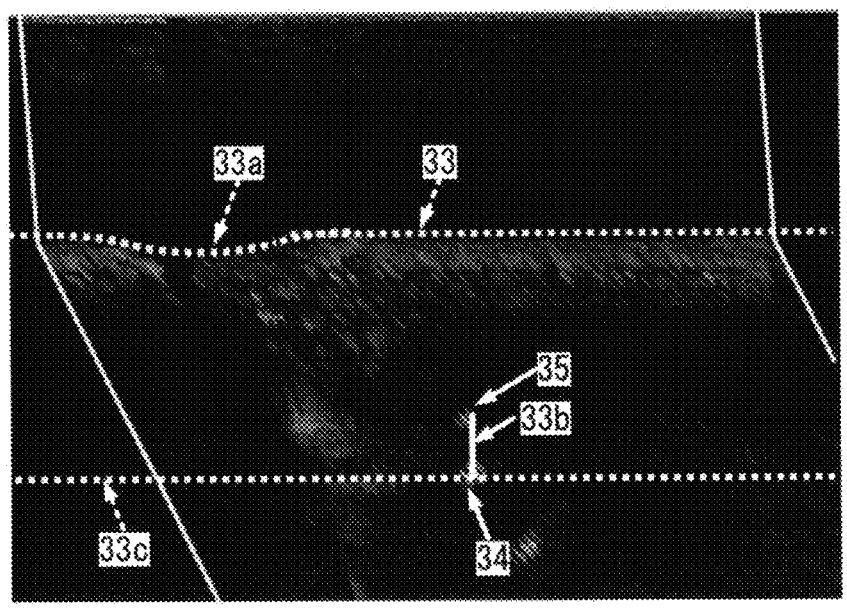
FIG. 23 is a diagram showing a result of performing reconstruction, taking the surface shape of an object into consideration.

FIG. 22 is a diagram showing a result of performing the reconstruction without taking the surface shape of the object into consideration. FIG. 23 is a diagram showing a result of performing the reconstruction, taking the surface shape of the object into consideration.

In these examples, the flaw detection is conducted under the condition that an ultrasonic wave is transmitted from a curved surface (an undulation) 33a on a flaw detection surface 33 of the object to a flaw 33b given to the object.

As shown in FIG. 22, the entire flaw 33b is the position where the influence of the curved surface 33a is exerted, but an indication of a corner echo 34 which is an echo from an opening of the flaw 33b occurring in a back surface 33c opposite the flaw detection surface 33 of the object is extended in an art shape. Furthermore, it can also be seen that a peak showing the corner echo 34 is positioned at an inner side than the surface of the back surface 33c. In addition, a tip echo 35 which is an echo from a tip of the flaw 33b on the inside of the object does not show a distinct peak. Furthermore, in FIG. 22, there is a region showing an echo at a position where the flaw 33b does not exist (on the left side of the diagram).

On the other hand, in FIG. 23, the position of the corner echo 34 is clearer compared to FIG. 22. In addition, the position of the peak is distinct for both the corner echo 34 and the tip echo 35, and the error in the position is greatly reduced.

As described, with reconstruction that does not take the surface shape into consideration, indications of the corner echo 34 and the tip echo 35 of the flaw 33b given to the inside of the object which receives the influence of the curved surface 33a are unclear, and also, the indication position of the flaw 33b includes an error with respect to the actual position of the flaw 33b.

In contrast, with reconstruction that takes the surface shape into consideration, the indications of the corner echo 34 and the tip echo 35 of the flaw 33b are shown clearly, and also, the indication position of the flaw 33b is accurate.

As described, the ultrasonic flaw detector 1 of the present embodiment and the flaw detection method are capable of conducting accurate ultrasonic flaw detection by conducting flaw detection according to the surface shape of an object and reconstructing the flaw detection result according to the surface shape. The ultrasonic flaw detector 1 and the flaw detection method can thereby conduct the ultrasonic flaw detection with high detection accuracy on the surface of an object having a complex shape.

In addition, in the ultrasonic flaw detection, a difference in sensitivity may occur depending on the surface shape of the object due to the angle of beam spread of the ultrasonic wave, the transmittance obtained based on the relation between the inclination θj and the incident angle αj, and the like. This means that the flaw detection accuracy varies depending on the influence of the surface shape of the object, and may lead to a significant measurement error.

Thus, the ultrasonic flaw detector 1 and the flaw detection method of the present embodiment may perform calculation based on the surface shape of the object and the angle of beam spread of the ultrasonic wave and may maintain the intensity of the incident waves converging on the focal point to be constant.

Figure 24:
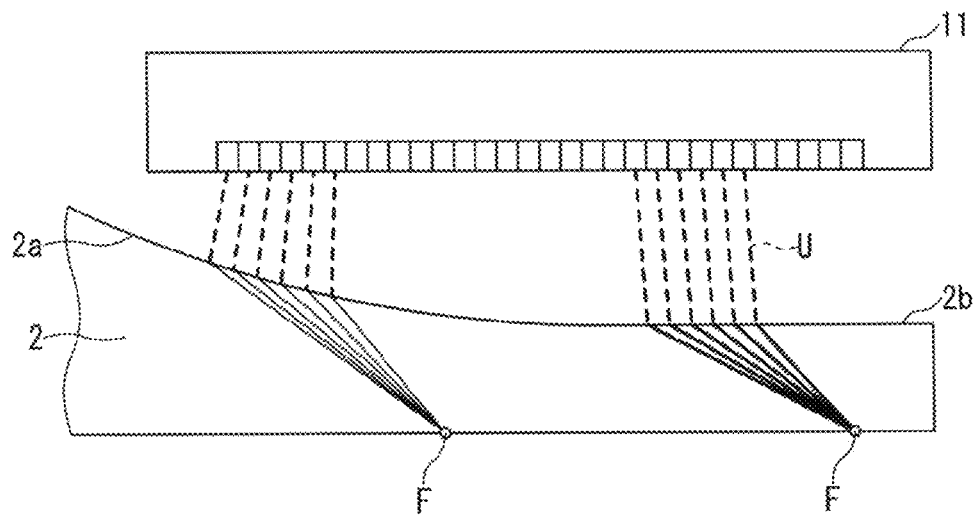
FIG. 24 is an explanatory diagram of a case where a difference in sensitivity arises due to a difference between surface shapes of a pipe.

FIG. 24 is an explanatory diagram representing a case where a difference in sensitivity arises due to a difference between surface shapes of the pipe 2.

Figure 25:
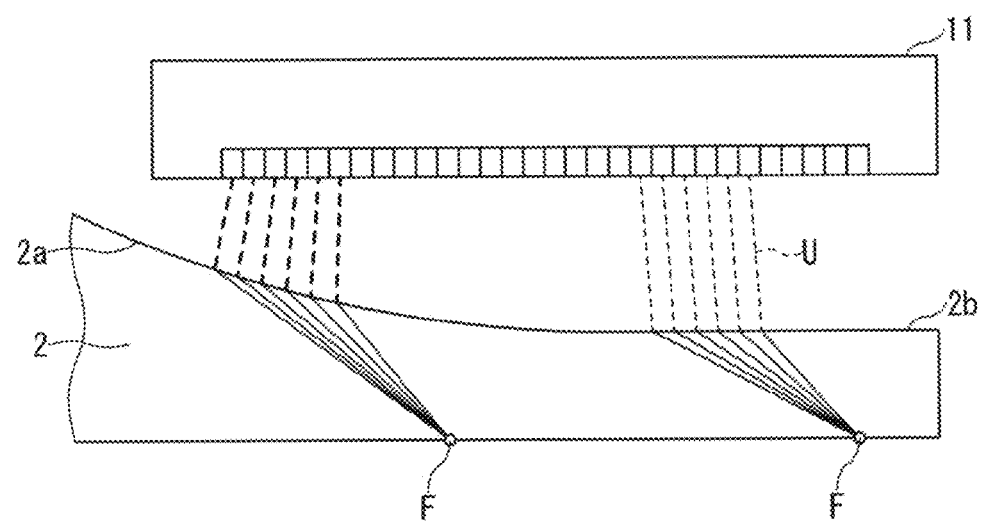
FIG. 25 is an explanatory diagram of a case where a gain of an ultrasonic wave U is adjusted according to the surface shape of a pipe.

In the illustrations of FIGS. 24 and 25, the difference in the intensity of an ultrasonic wave U is expressed by the thickness of the line (dotted line) representing the ultrasonic wave U.

The intensity of an ultrasonic wave U entering the planar surface 2b of the pipe 2 is greater than that of an ultrasonic wave U entering the curved surface 2a, and the difference in the incident points on the curved surface 2a and the planar surface 2b results in the difference in the flaw detection accuracy.

Accordingly, for example, the gain of an ultrasonic wave oscillated from an ultrasonic element that is used is increased in advance for a surface shape with the lowest sensitivity, or by taking the surface shape with the lowest sensitivity in consideration, the gain of an ultrasonic wave entering a surface shape at which the sensitivity is not easily reduced is lowered in advance.

FIG. 25 is an explanatory diagram of a case where the gain of the ultrasonic wave U is adjusted according to the surface shape of the pipe 2.

According to the surface shape of the pipe 2, the ultrasonic flaw detector 1 lowers, in advance, the gain of an ultrasonic wave U having an incident point being on the planar surface 2b with a high sensitivity. The intensity of the ultrasonic wave U inside the pipe 2 thereby becomes almost equal for the curved surface 2a and the planar surface 2b.

Furthermore, the number of ultrasonic elements that are simultaneously driven is increased more than a normal case with respect to a surface shape with a lower sensitivity.

Figure 26:
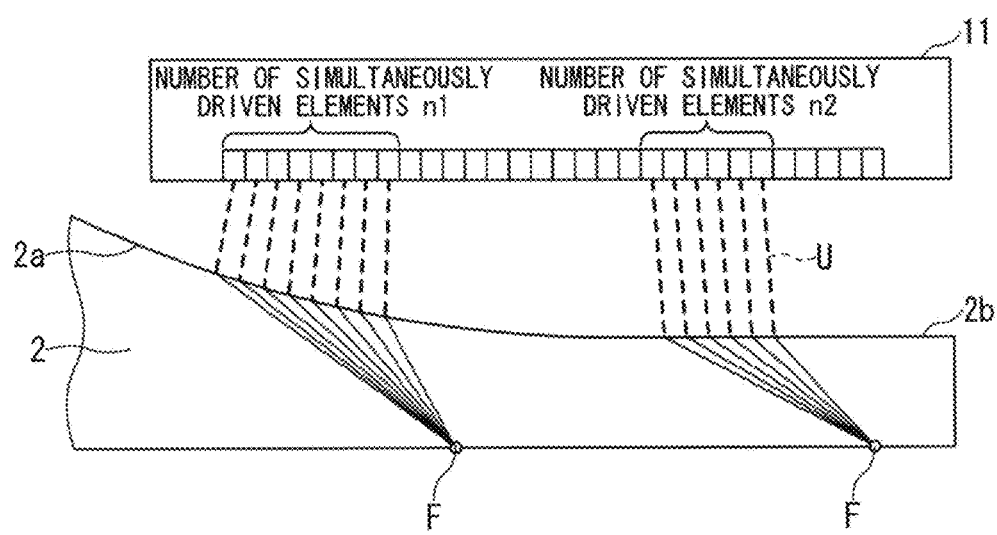
FIG. 26 is an explanatory diagram of a case where the number of simultaneously driven elements is adjusted according to the surface shape of a pipe.

FIG. 26 is an explanatory diagram of a case where the number of simultaneously driven elements is adjusted according to the surface shape of the pipe 2.

The ultrasonic flaw detector 1 has increased the number 'n1' of the ultrasonic elements that oscillate the ultrasonic waves that are emitted on the curved surface 2a than the number 'n2' of the ultrasonic elements that oscillate the ultrasonic waves whose incident points are on the planar surface 2b. The intensity of the ultrasonic wave U inside the pipe 2 thereby becomes almost equal for the curved surface 2a and the planar surface 2b.

The method of estimating the ultrasonic intensity at a focal point F may include a general ray tracing method, or other numerical analysis methods such as a difference method, a finite-element method, an FDTD method and a CIP method.

Hereinbefore, although several embodiments of the present invention have been described, these embodiments are presented as examples and are not intended to limit the scope of the invention. These new embodiments can be conducted in other various modes, and various omissions, replacements and modifications can be made insofar as they do not depart from the spirit of the invention. These embodiments and modifications are within the scope and spirit of the present invention and also within the scope of the claims and equivalents thereof.

For example, the ultrasonic flaw detector 1 and the flaw detection method may be adopted with other flaw detecting methods such as sector scan, which scans the refraction angle fanwise, and Dynamic Depth Focusing (DDF), which changes the focal point depth according to an area to be measured.

Figure 27:
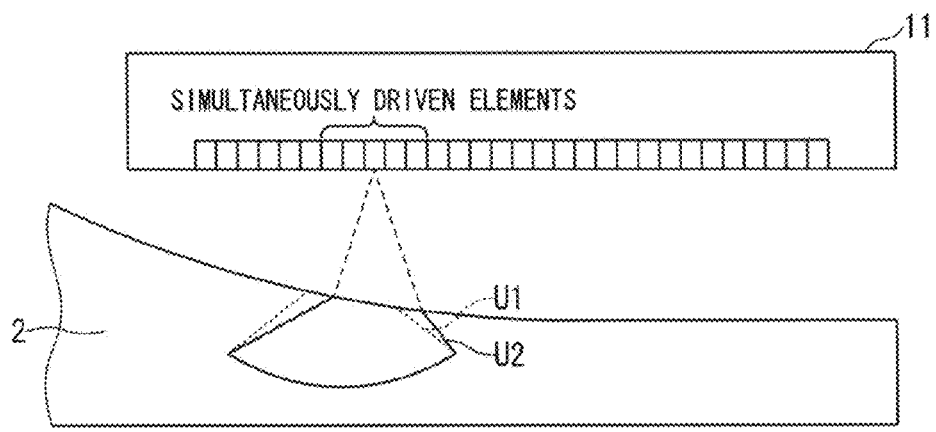
FIG. 27 is an explanatory diagram of a case where a sector scan is applied to ultrasonic flaw detection without taking the surface shape of a pipe into consideration.
Figure 28:
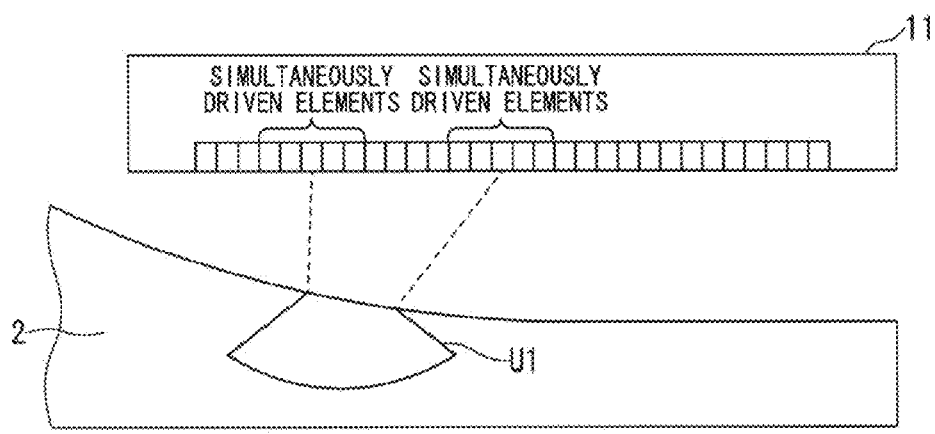
FIG. 28 is an explanatory diagram of a case where a sector scan is applied to ultrasonic flaw detection, taking the surface shape of a pipe into consideration.

FIG. 27 is an explanatory diagram of a case where the sector scan is applied to ultrasonic flaw detection without taking the surface shape of the pipe 2 into consideration. FIG. 28 is an explanatory diagram of a case where the sector scan is applied to ultrasonic flaw detection, taking the surface shape of the pipe 2 into consideration.

In the case the surface shape of the pipe 2 is planar, ultrasonic waves ideally enter the pipe 2 like the ultrasonic waves U1 shown by dotted lines in FIG. 27. However, if the surface shape of the pipe 2 is curved, ultrasonic waves do not enter from intended positions, and the ultrasonic waves enter the pipe 2 like the ultrasonic waves U2 shown by solid lines in FIG. 27. As a result, the flaw detection range will not take an ideal fan shape, and hence, the flaw detection cannot be conducted accurately.

In contrast, the ultrasonic flaw detector of the present embodiment and its method take the surface shape of the pipe 2 into consideration, and perform the back calculation of the simultaneously driven elements from the flaw detection range having an ideal fan shape of the ultrasonic waves U1 shown in FIG. 27. It therefore becomes possible, as shown in FIG. 28, to conduct the ideal flaw detection even if the surface shape is curved, as in a case where the surface shape is planar.

Furthermore, the analysis unit 15 and the calculation unit 18 can be realized, in each embodiment, by a processing unit, a memory, a program for causing these to operation, and the like. Accordingly, although the analysis unit 15 and the calculation unit 18 have been described as separate structural elements, they can also be integrated into one piece of hardware.

What is claimed is:

1. An ultrasonic flaw detector comprising:
an ultrasonic probe that emits an ultrasonic wave on an object to be inspected and receives a reflected ultrasonic wave from the object;
circuitry configured to control a plurality of ultrasonic elements to emit an ultrasonic wave from the ultrasonic probe and to control a reflected ultrasonic wave from the object; and
a design database that stores in advance data on a surface shape of a surface of the object; wherein
the circuitry is configured to adjust a number of the plurality of ultrasonic elements to be driven based on the surface shape stored in the design database and to calculate a plurality of incident positions on the surface of the object where the ultrasonic wave enters based on a refraction angle of the ultrasonic wave in the object and the surface shape.

2. The ultrasonic flaw detector according to claim 1, wherein the circuitry is configured to calculate and obtain the incident position based on the refraction angle and a focal point of the ultrasonic wave in a case of driving the ultrasonic element under flaw detection conditions for being used for the object having a planar surface shape.

3. The ultrasonic flaw detector according to claim 1, wherein the surface shape is a surface inclination of the object with respect to the ultrasonic probe.

4. The ultrasonic flaw detector according to claim 1, wherein the circuitry is configured to control a gain of an ultrasonic wave transmitted from the ultrasonic element according to the surface shape.

5. The ultrasonic flaw detector according to claim 1, wherein the circuitry is configured to control the number of simultaneously driven ultrasonic elements according to the surface shape.

6. The ultrasonic flaw detector according to claim 1, wherein the circuitry is configured to control a gain of an ultrasonic wave transmitted from the ultrasonic element, according to the surface shape and control the number of simultaneously driven ultrasonic elements according to the surface shape.

7. The ultrasonic flaw detector according to claim 1, wherein the circuitry is configured to perform signal processing of an ultrasonic wave transmitted/received by the ultrasonic probe and measures the surface shape of the object.

8. An ultrasonic flaw detecting method comprising:
   emitting an ultrasonic wave on an object to be inspected by driving a plurality of ultrasonic elements and receiving a reflected ultrasonic wave from the object;
   determining a refraction angle of the ultrasonic wave incident in the object;
   acquiring a surface shape of a surface of the object at the incident position from a design database that stores in advance data on the surface shape of the surface of the object;
   calculating a plurality of incident positions on the surface of the object where the ultrasonic wave enters based on the refraction angle and the surface shape;
   obtaining an incident angle of the ultrasonic wave entering at each of the plurality of incident positions; and
   adjusting a number of a plurality of ultrasonic elements to be driven based on each of the plurality of incident positions and the incident angle at said each of the plurality of incident positions.

* * * * *